(12) United States Patent
Feiertag

(10) Patent No.: US 10,188,283 B2
(45) Date of Patent: Jan. 29, 2019

(54) TRIAL FRAME

(71) Applicant: Oculus Optikgeraete GmbH, Wetzlar (DE)

(72) Inventor: Carsten Feiertag, Hungen (DE)

(73) Assignee: OCULUS OPTIKGERAETE GMBH, Wetzlar (DE)

( * ) Notice: Subject to any disclaimer, the term of this patent is extended or adjusted under 35 U.S.C. 154(b) by 83 days.

(21) Appl. No.: 15/374,589

(22) Filed: Dec. 9, 2016

(65) Prior Publication Data

US 2017/0164823 A1 Jun. 15, 2017

(30) Foreign Application Priority Data

Dec. 11, 2015 (DE) .................. 20 2015 106 765

(51) Int. Cl.
| | | |
|---|---|---|
| *A61B 3/02* | (2006.01) | |
| *A61B 3/04* | (2006.01) | |
| *A61B 3/00* | (2006.01) | |
| *G02B 5/30* | (2006.01) | |

(52) U.S. Cl.
CPC .............. *A61B 3/04* (2013.01); *A61B 3/0075* (2013.01); *G02B 5/3025* (2013.01)

(58) Field of Classification Search
CPC ........ G02C 7/10; G02C 13/003; G02C 5/126; G02C 5/143; G02C 7/061; G02C 7/102; G02C 7/108; G02C 7/12; A61B 3/02
USPC ..... 351/229, 222, 49, 57, 59, 118, 119, 124, 351/128, 137, 158, 204
See application file for complete search history.

(56) References Cited

U.S. PATENT DOCUMENTS 5,742,375 A * 4/1998 Szirth .................. A61B 3/04
351/227

FOREIGN PATENT DOCUMENTS

| DE | 9205768 U1 | 11/1992 |
|---|---|---|
| DE | 202015001203 U1 | 3/2015 |
| EP | 0567817 B1 | 1/1996 |
| JP | 2009112400 A | 5/2009 |

OTHER PUBLICATIONS

European Search Report in connection with EP 16 20 2575 in the name of Oculus Optikgeräte GmbH, dated May 4, 2017.

* cited by examiner

*Primary Examiner* — Hung Dang
(74) *Attorney, Agent, or Firm* — Quarles & Brady LLP

(57) ABSTRACT

The invention relates to a trial frame for determining the subjective refraction of a subject, comprising two lens holder devices for receiving lenses, a bridge, which adjustably connects the lens holder devices, a nose rest device having a pivotable and height-adjustable nose rest and two temples, which are adjustable in length and height, the trial frame comprising two polarization filter devices, the polarization filter devices having a circular or a linear polarization filter, a pivot for pivoting the circular or linear polarization filter in and out in front of the lens holder device, and a rotating device for rotating the polarization filter in front of the lens holder device, the polarization filter devices each being removably attachable to the lens holder devices.

19 Claims, 7 Drawing Sheets

Fig. 10
Fig. 9
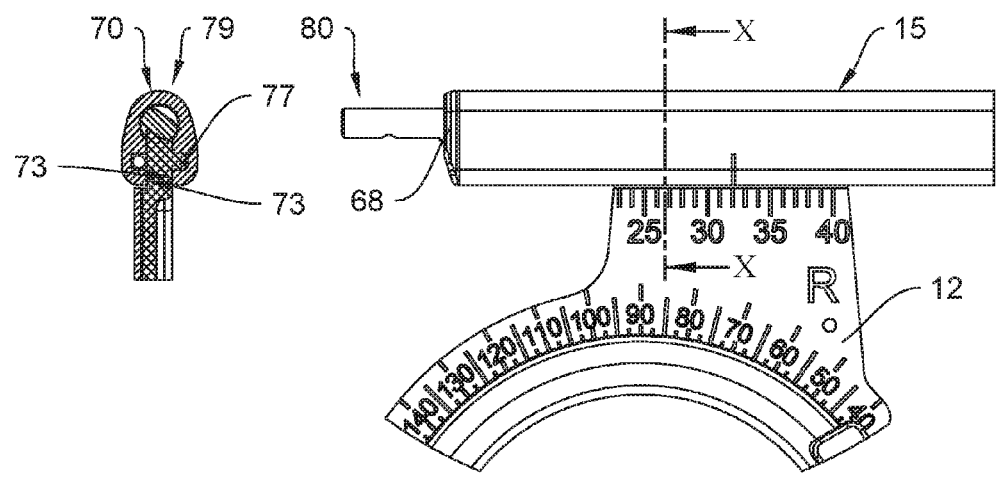
Fig. 11
Fig. 12
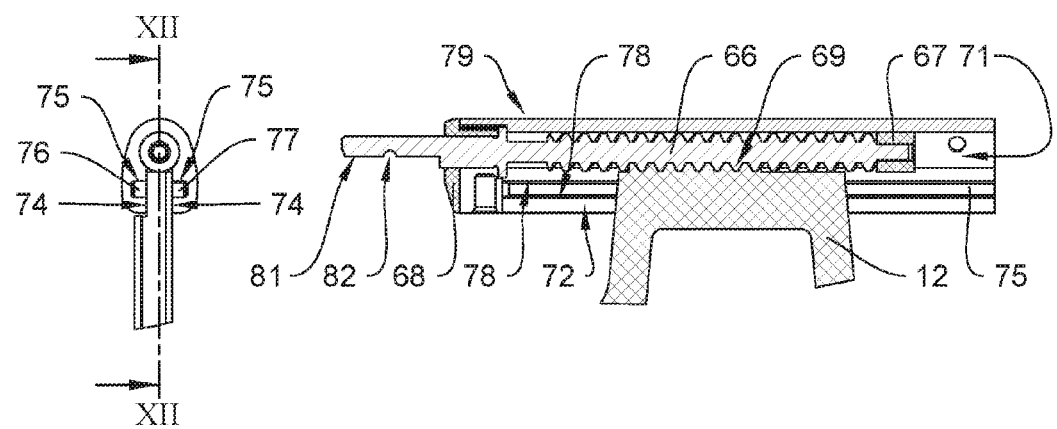

Fig. 13
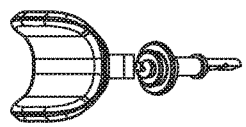
Fig. 14
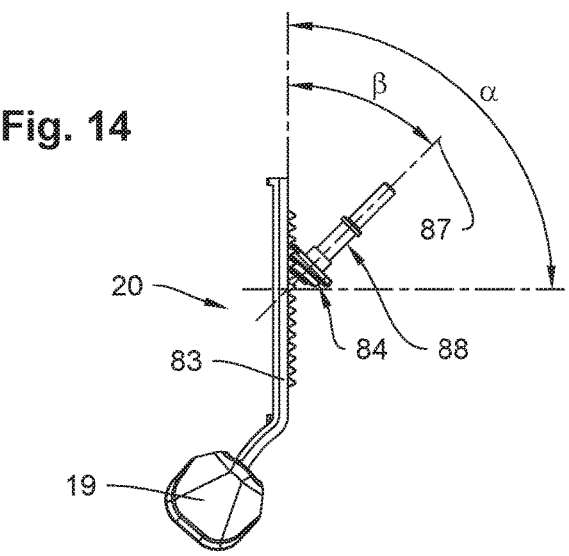
Fig. 15
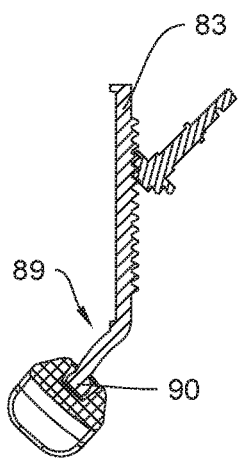
Fig. 16

TRIAL FRAME

CROSS-REFERENCE TO RELATED APPLICATIONS

This application claims the benefit of German Utility Model Application No. 20 2015 106 765.8 filed Dec. 11, 2015. The contents of which is hereby incorporated by reference as if set forth in its entirety herein.

FIELD OF THE INVENTION

The invention relates to a trial frame for determining the subjective refraction of a subject, comprising two lens holder devices for receiving insert lenses, a bridge, which connects the lens holder devices in such a manner that their distance relative to each other is adjustable, a nose rest device having a pivotable and height-adjustable nose rest, and two temples, which are adjustable in length and height, the nose rest device having an adjustment gear for adjusting the height of the nose rest.

BACKGROUND OF THE INVENTION

Trial frames of this kind are typically used to determine ophthalmic lenses. To do so, the trial frame is adjusted to a subject, that is a person, and easily exchangeable insert lenses or trial lenses are inserted into the trial frame. The insert lenses are arranged in a rotatable manner so as to be able to correct astigmatic defects in their axial position. Lateral defects and height defects, which are corrected by means of prisms, have to be adjustable as well, which is why the trial frame has to be precisely adjusted to a subject or patient. For example, a pupil distance has to be adjustable, wherein a pupil center of each eye is supposed to be adjustable in a separate manner. A height of the trial frame is adjusted via the nose rest, which is also arranged on the bridge in a pivotable manner. By pivoting the nose rest and adjusting the length of the temples, a distance of the trial frame in relation to the eyes can be adjusted. For adjustment to different ear shapes, the temples are pivotable in height and laterally. A trial frame of this kind is known from EP 0 567 817 B1, for instance.

Since the examining person will always adjust the trial frame immediately on the head of the subject, the operating elements of the trial frame have to be easy to operate and they need to be arranged in a manner that allows ergonomic handling. At the same time, the subject should not be unnecessarily bothered by the operation of the trial frame during adjustment of the trial frame. For instance, catching of the subject's hair in the trial frame and hand movements within the closer field of vision are undesired.

Because of the various adjustment options, the known trial frames are composed of a plurality of individual parts, which makes manufacture of the trial frame complex. For instance, height adjustability of the nose rest typically requires an adjustment gear, said adjustment gear being composed of a plurality of gear elements or gear wheels for converting a rotational adjusting motion into a translational motion of the nose rest at a desired gear ratio.

With the known trial frames, the lens holder devices are displaced by means of threaded spindles arranged within the bridge in order to adjust the pupil distance. For this purpose, spindle nuts are formed or arranged on the lens holder devices. For instance, it is known for a lens holder device to be produced in a plastic injection-molding process and for the threaded nut to be molded to the lens holder device. To do so, a threaded spindle is injection-coated in a mold, the threaded spindle having to be unscrewed from the threaded nut in order to demold the lens holder device. Because of cooling or mold shrinkage of the plastic material, however, the threaded nut may become deformed in such a manner that a thread for the threaded spindle will have to be rethreaded.

Also, in the case of some trial frames, the bridge is made of a metal tube into which a groove is milled. Inner flanks of this groove serve as a longitudinal guide for the lens holder devices, allowing the lens holder devices to be transversally displaced. The guide means thus formed has to exhibit a comparatively precise fit in order to preclude sagittal tilting of the lens holder as far as possible. Hence, after milling of the groove, the bridge has to be routinely refinished in order to form the desired loose fit. These necessary manufacturing steps, too, are relatively time-consuming.

Trial frames are also employed together with polarization filter devices, which can be used for eyesight tests in combination with a polarized display of optotypes. Depending on the type of polarization of the optotypes, circular or linear, corresponding polarization filters are needed on the trial frame. However, these polarization filters require different handling, which means that the trial frame has to be designed according to said handling.

SUMMARY OF THE INVENTION

Therefore, the object of the present invention is to provide a trial frame that is flexible in use.

The trial frame according to the invention for determining the subjective refraction of a subject comprises two lens holder devices for receiving insert lenses, a bridge, which connects the lens holder devices in such a manner that their distance relative to each other is adjustable, a nose rest device having a pivotable and height-adjustable nose rest, and two temples, which are adjustable in length and height, the trial frame comprising two polarization filter devices, the polarization filter devices having a circular or a linear polarization filter, wherein the polarization filter devices having the circular or linear polarization filter each have a pivot means for pivoting the circular or linear polarization filter in and out in front of the lens holder device, the polarization filter devices having the linear polarization filter each having a rotating means for rotating the linear polarization filter in front of the lens holder device, the polarization filter devices each being removably attachable to the lens holder devices by means of a locking connection.

The positional and directional terms indicated below always relate to the body or the body planes of a subject or patient to whom the trial frame is adjusted.

Depending on the polarization of optotypes used, the circular or the linear polarization filter can be selected. The circular and the linear polarization filter can each be pivoted into or out of a subject's field of vision in front of the lens holder device by means of the pivot means in order to be able to perform the corresponding eyesight test. If the polarization filter device is equipped with the linear polarization filter, the rotating means is further provided to rotate the linear polarization filter in front of the lens holder device or the subject's field of vision. The pivot means can be realized with a hinge that allows radial or axial pivoting of the polarization filter relative to the subject's optical axis. The rotating means can be realized with an axis that allows radial or axial rotating of the linear polarization filter relative to the subject's optical axis. This allows changing an orientation or direction of polarization. Thus, use of the polarization filter devices is flexible depending on the polarization of the optotypes.

Since the polarization filter devices are supposed to be usable for optional eyesight tests with the trial frame, they can be removably attached to the trial frame independently of the lens holder devices. Owing to the fact that this removable attachment happens by means of a locking connection on the lens holder device, the polarization filter device can be attached and removed again in a particularly quick and simple manner. The locking connection can also be designed in such a manner that a clamping force is effected, which prevents undesired motion of the polarization filter device on the lens holder device. In this case, the locking connection can be realized as a zero-play connection, allowing the polarization filter device to be operated in a particularly precise manner.

At an attachment end of a holder of the polarization filter device, a one-piece spring clamp can be formed, which can engage behind a crosspiece molded to the lens holder device, wherein an actuating lever can be molded to the spring clamp or to the attachment end by means of which the spring clamp can be opened. The attachment end can also be in one piece and can be made entirely of plastic and can comprise the spring clamp so as to reduce a number of parts of the trial frame even further. The attachment end can also be realized in the shape of a claw that engages behind the crosspiece in such a manner that the holder can be hooked onto the crosspiece. Furthermore, a locking nose or locking recess can be molded to the crosspiece or to the spring clamp, into which a matching locking recess or locking nose can engage. When the claw engages the crosspiece at an edge thereof or is hooked into the crosspiece at said edge, the spring clamp can engage an opposite edge of the crosspiece and lock with it. To simplify detachment of the holder and of the spring clamp from the lens holder device and from the crosspiece, respectively, the actuating lever can be molded to the spring clamp or to the attachment end. The actuating lever can be arranged in such a manner that the spring clamp is bent open and the locking connection is released when the actuating lever is actuated.

The nose rest device can have an adjustment gear for adjusting the height of the nose rest, wherein the adjustment gear can have a toothed rack and a bevel worm wheel, which are engaged with each other. Owing to the fact that the adjustment gear for adjusting the height of the nose rest has a toothed rack, the toothed rack can be moved translationally, thus effecting a height adjustment of the nose rest. Furthermore, the toothed rack easily allows the adjustment gear to be self-locking. The toothed rack is engaged with the bevel worm wheel, so that the rotation of the bevel worm wheel causes the translational motion of the toothed rack. Owing to the fact that, with respect to a longitudinal axis of the bevel worm wheel, the bevel worm wheel forms a conical outer diameter with teeth, the bevel worm wheel can be arranged relative to the toothed rack in such a manner that the longitudinal axis of the bevel worm wheel is arranged at an angle $\beta$, which corresponds to half an opening angle $\alpha$ of the bevel worm wheel. In the case of a longitudinal height adjustment of the toothed rack or in the case of a nose rest height-adjustable in a sagittal plane relative to the bridge or lens holder device, the bevel worm wheel will preferably arranged in such a manner that the longitudinal axis extends in a distal direction. In this way, it becomes possible to adjust the height of the nose rest without a hand of the operator entering the immediate field of vision of a subject or patient. Moreover, insertion of insert lenses into the lens holder device is not impeded by an operating element of the adjustment gear in the immediate area of the nose of the subject. The trial frame is thus easier to handle and is less bothersome to the subject.

The adjustment gear can be formed by the toothed rack and the bevel worm wheel. In this case, the adjustment gear is formed by only two mobile gear components. Thus, installation of the adjustment gear is substantially simplified, which allows cost-effective manufacture of the trial frame. The teeth of the bevel worm wheel can thus run in the manner of a conical thread. Since the nose rest is adjusted manually, only low forces are transmitted via the adjustment gear, which is why simplified geometries can be used for forming teeth or a teeth geometry of the toothed rack and of the bevel worm wheel.

It is particularly advantageous for the bevel worm wheel to have an opening angle $\alpha$ of 60° to 120°, preferably of 90°. When the bevel worm wheel is then engaged with the toothed rack, the bevel worm wheel is inclined relative to the toothed rack by an angle $\beta$ of 30° to 60°, preferably of 45°. Since the toothed rack is substantially adjusted in a longitudinal direction, it is further advantageous for the bevel worm wheel to be arranged on the toothed rack in such a manner that it is inclined in a distal direction or upward, allowing an operating element in connection with the bevel worm wheel to be arranged above a subject's nasal bridge. When the nose rest is being adjusted by an operator, the operator's actuating hand will thus not be located immediately in front of the subject's eyes or within the closer field of vision. Moreover, the operating element will thus be arranged in a manner that is ergonomically favorable to the operator and will not be in the way when the insert lenses are being exchanged.

Furthermore, the bevel worm wheel can have a lead of 1 mm to 3 mm, preferably of 2 mm. Thus, the nose rest can be adjusted by the corresponding length in a longitudinal direction with a single revolution of an operating element of the nose rest device.

The bevel worm wheel can be molded to an actuating shaft, wherein the actuating shaft can then be realized in such a manner that an operating element can be plugged directly onto the actuating shaft. For example, the bevel worm wheel can be produced in one piece in an injection-molding process. Hence, the bevel worm wheel can be made of plastic or metal. Overall, a number of parts of the trial frame can thus be reduced further. A distal end of the actuating shaft can be realized in such a manner that the operating element can be connected to the distal end in a form-fitting manner. For example, a material recess in the shape of a segment of a circle can be realized at the distal end, to which the operating element is fitted. Furthermore, a locking recess or a locking protrusion for a locking connection to the operating element can be realized at the distal end.

In this way, the operating element can also be arranged above the bridge, the operating element thus being arranged at the edge or outside of a subject's field of vision.

Operating elements of the trial frame can be actuated particularly well if they are cylindrical or frustoconical and made in one piece of a flexible plastic material. In particular when taking hold of a frustoconical operating element by pronating 2 to 3 fingers, the operating element can be gripped at the largest diameter of the frustum when performing fine adjustment or optionally at the circumferential surface of the frustum when performing quick adjustment. Moreover, owing to the flexible plastic material, the operating element can be grasped in a haptically pleasant manner and slipping of the operating element through the fingers is prevented. Owing to the one-piece design, production of the operating element is cost-effective and a number of parts of the trial frame is reduced. For connecting the operating element to the actuating shafts or spindles of the trial frame, the operating element can have a recess for form-fitting plugging with a locking protrusion or a locking recess.

The nose rest device can be mounted on a pivot axis of the bridge by means of a radial clamping. A radial clamping can be produced in a particularly simple manner and can have a ring, for example, which surrounds the pivot axis and has a slot or a spring. The radial clamping can also be adjustable in terms of its clamping force. The substantial aspect is that there is a self-locking clamping of the nose rest device on the pivot axis.

The bridge can be formed by two bridge sections, which can be firmly connected by means of a pivot axis, wherein the nose rest device can be pivotably mounted on the pivot axis. In a particularly simple embodiment, the bridge sections can then be connected merely by means of a pin, which is inserted into the respective bridge sections and forms the pivot axis. In this case, the outer shape of the bridge sections can be formed independently of the pivot axis or of the connection to the nose rest device. The bridge sections can be secured to the pivot axis against turning or against the pivot axis being pulled out simply by means of a screw or by being glued. In this case, it is also particularly advantageous if there is solely an axial clamping of the nose rest device on the pivot axis.

The bridge and the lens holder devices together can form a guide means for guiding the mobile lens holder devices in the longitudinal direction of the bridge, wherein the bridge can have a spindle gear, which can be self-locking and can have a threaded spindle for adjusting the distance of the lens holder devices, wherein at least one guide protrusion can be formed on each of the lens holder devices, said guide protrusion being able to engage into a guide groove formed in the bridge, wherein open threaded sections can be formed on the lens holder devices, wherein the threaded spindle can be engaged with the threaded section. Thus, the guide means can be realized in such a manner that the lens holder devices are mobile in the longitudinal direction of the bridge, i.e. transversally mobile. In this way, it becomes possible to adjust a relative distance of the lens holder devices so as to adjust the trial frame to a pupil distance. This distance adjustment can take place via the spindle gear, which has at least one threaded spindle. There may be a single threaded spindle with opposite threads in threaded sections for both lens holder devices or each lens holder device may have its own threaded spindle. The threaded spindle will then engage into a threaded section of the lens holder device, wherein the threaded section can be open, which means that the threaded section is realized in the manner of a toothed rack or has a sector of a threaded bore at the lens holder device. In that case, the threaded section can be formed integrally with the lens holder device, for instance in one piece by injection molding. By means of a rotational motion of the threaded spindle, a translational motion of the lens holder device along a longitudinal axis of the bridge can be caused. Cumbersome demolding of the lens holder device or a potentially required rethreading of the threaded section is no longer necessary. The guide protrusion can also be molded to the lens holder device. The guide protrusion can preferably be arranged on a side surface of the lens holder device, wherein another guide protrusion can also be arranged on an opposite side surface or multiple guide protrusions can be arranged on one side surface. The substantial aspect is that the guide protrusion engages into the guide groove which can be formed in the bridge. Aside from guide surfaces of the guide means, which can be in contact with side surfaces of the lens holder device, the guide protrusion and the guide groove form other guide surfaces, which can ensure a substantially zero-play guiding of the lens holder devices in the bridge. Radial tilting of the lens holder devices relative to the threaded spindle, as known from the state of the art, can be effectively prevented in this way.

The bridge can have a longitudinal slot which forms parallel guide surfaces for the lens holder devices, wherein the guide groove can be formed on or in at least one of the guide surfaces. The guide surfaces of the longitudinal slot can then be in contact with side surfaces of the lens holder devices. A longitudinal slot can be formed in one of the guide surfaces or also in both guide surfaces, wherein the longitudinal slot can be formed to match the guide protrusion or guide protrusions. The guide groove can be formed in the manner of a rectangular tapering or semicircular groove. The guide grove consequently also prevents the lens holder devices from dropping out of the longitudinal slot. Sagittal tilting of the lens holder devices can be effectively prevented in particular by the horizontal guide surfaces of the guide means formed between the guide groove and the guide protrusion. A particular accuracy of fit of the longitudinal slot is no longer required in this case.

In particular, a passage bore for receiving the threaded spindle can be formed in the longitudinal direction of the bridge, the passage bore being adjacent to the longitudinal slot. The longitudinal slot thus protrudes into the passage bore, and a diameter of the passage bore can be the same as or larger than a width of the longitudinal slot. Also, assembly of the trial frame is substantially simplified by the fact that the threaded spindle has to be inserted into the passage bore with the longitudinal slot together with the lens holder device.

It is particularly advantageous if a plurality of crosspiece-shaped guide protrusions is formed on the lens holder device. The crosspiece-shaped guide protrusions can be arranged on both side surfaces of the lens holder device. For example, two spaced-apart crosspiece-shaped guide protrusions can be arranged or formed on one side surface and a single crosspiece-shaped guide protrusion can be arranged or formed on an opposite side surface. The resulting rest of the lens holder device on three support points of the guide means prevents the lens holder device from becoming wedged or jammed in the guide groove.

Production of the trial frame becomes especially cost-effective if the bridge is formed by an extruded profile. The extruded profile can advantageously have the cross-section of the bridge from the start, thus requiring no finishing work or only insignificant finishing work on the extruded profile. Since there may consequently be no need for milling work on the extruded profile, the problem of bending open the longitudinal slot is avoided. Moreover, an extruded profile made of aluminum or titanium, for example, is available at low cost.

The threaded spindle can be mounted radially on an inner bearing and radially and axially on an outer bearing. Hence, the inner bearing can be realized as a loose bearing and the outer bearing can be realized as a fixed bearing of the threaded spindle. The inner bearing can be a plastic bushing, which is merely inserted into a bore in the bridge for receiving the threaded spindle. The outer bearing can be made of plastic, wherein the outer bearing can be firmly fixed to an outer transversal end of the bridge. This way of mounting the threaded spindle is made necessary by, among other things, the fact that the lens holder device does not have a closed thread. In case the inner bearing is merely a plastic bushing, its added costs are easily compensated for by the simplified demolding of the lens holder device alone.

The outer bearing can engage into the guide groove in a form-fitting manner. Thus, it is possible to prevent radial rotation of the outer bearing and to also secure the outer bearing against axial motions, for instance by means of a clamping fit in the guide groove. Optionally, it may also be envisaged for the outer bearing to be fixed to the bridge by a screw connection. The outer bearing can be produced by plastic injection molding.

The lens holder device can have a rotatable ring on which lens seats are formed, wherein an actuating shaft of a ring can have an adjustable braking means, wherein the braking means can be an eccentric plastic ring. The rotatable ring having the lens seats can be made of plastic or light metal, wherein a gear wheel of the actuating shaft can engage into teeth formed on the rotatable ring, the rotatable ring thus being rotatable by means of a rotation of the actuating shaft. In this case, the actuating shaft is arranged in such a manner that it extends in the direction of a center of the ring. To prevent unintentional rotation of the ring, the plastic ring can surround the actuating shaft so that a rotation resistance of the actuating shaft can be formed. In case the plastic ring is eccentric, a larger or a smaller rotation resistance can be set as needed through radial rotation of the plastic ring on the actuating shaft.

The lens holder devices can each have four front and two rear lens seats. The plurality of front or ventral and rear or dorsal lens seats offers particularly versatile usage of the trial frame. For instance, a series of insert lenses, for correcting short-sightedness, long-sightedness and astigmatism, for example, can be used simultaneously. The lens seats can each be formed by at least two or three crosspieces that can support the insert lenses at their circumference.

The lens seats of the lens holder devices can each have at least one pressure finger for clamping an insert lens, the respective pressure fingers being arranged in a row at the lens holder device and being subjectable to a contact pressure force via a shared leaf spring. In case the lens seats are realized in the shape of crosspieces, one pressure finger per insert lens can be formed or arranged on one of the crosspieces. From the state of the art, it is known for these pressure fingers to each be subjected to the contact pressure force by means of individual leg springs made of spring wire. In order to reduce a number of parts of the trial frame and to simplify assembly, it is hence advantageous to use a single leaf spring instead of a plurality of leg springs. This requires that the pressure fingers are always arranged adjacent and in a row on the lens holder device. The leaf spring can also be realized in such a manner that the leaf spring forms multiple finger-shaped leaf-spring sections, which each act on one pressure finger alone.

Temple ends of the temples can each be flexible, wherein each temple end can also be loop-shaped. The dorsal temple ends of the temples can advantageously form a sickle-shaped or crescent-shaped loop, which can engage behind an ear or an antihelix in order to thus prevent the trial frame from dropping from a subject's head. The loop-shaped design of the temples ends provides them with flexibility and allows them to adjust especially well to an ear, preventing pressure marks on the ear that would be uncomfortable to a subject. The flexible design of the temple ends is simplified if the temples ends are made of an at least partially flexible moldable plastic material.

Temple ends of the temples can each be made in one piece and of a soft and a comparatively hard plastic material. It may be envisaged for the dorsal temple ends to be made of the soft plastic material and for the temple itself to be made of the hard plastic material at least in sections. Manufacture of the temple by means of plastic injection molding will thus be cost-effective and simple. The soft plastic material can be flexible, thus preventing pressure marks on a subject's ear. At least one straight temple section adjacent to the dorsal temple end can then be made of the comparatively hard plastic material because this temple section also has to be comparatively stiff. The temple section can also end in a metal temple section towards a ventral, front temple end. Both temple sections can be designed in such a manner that they can be telescoped into each other.

A front or ventral end of the temple can be cranked. This allows the temple to be arranged on the lens holder devices as deeply as possible, i.e. in the proximal direction. An operator will thus be able to inspect the eyes from the side and to put insert lenses into rear lens seats without hindrance. Also, a distance between the trial frame and the eyes can thus be adjusted and measured more easily by the operator. Owing to the fact that the temple or its ventral end is cranked, the temple does not have to be significantly inclined in relation to a horizontal transversal plane, which means that the temple is adjustable to an ear as usual.

Hereinafter, a preferred embodiment of the trial frame is explained in more detail with the aid of the drawing.

BRIEF DESCRIPTION OF THE DRAWINGS

In the drawing:

FIG. 9 shows a partial illustration of a lens holder device on a bridge;
FIG. 10 shows a section view along line X-X of FIG. 9;
FIG. 11 shows a partial illustration of the lens holder device and of the bridge of FIG. 9 in a lateral view;
FIG. 12 shows a section view along line XII-XII of FIG. 11;
FIG. 13 shows a bottom view of a nose rest device;
FIG. 14 shows a lateral view of the nose rest device;
FIG. 15 shows a rear view of the nose rest device;
and
FIG. 16 shows a cross-section view of the nose rest device.

DETAILED DESCRIPTION OF THE INVENTION

Figure 1:
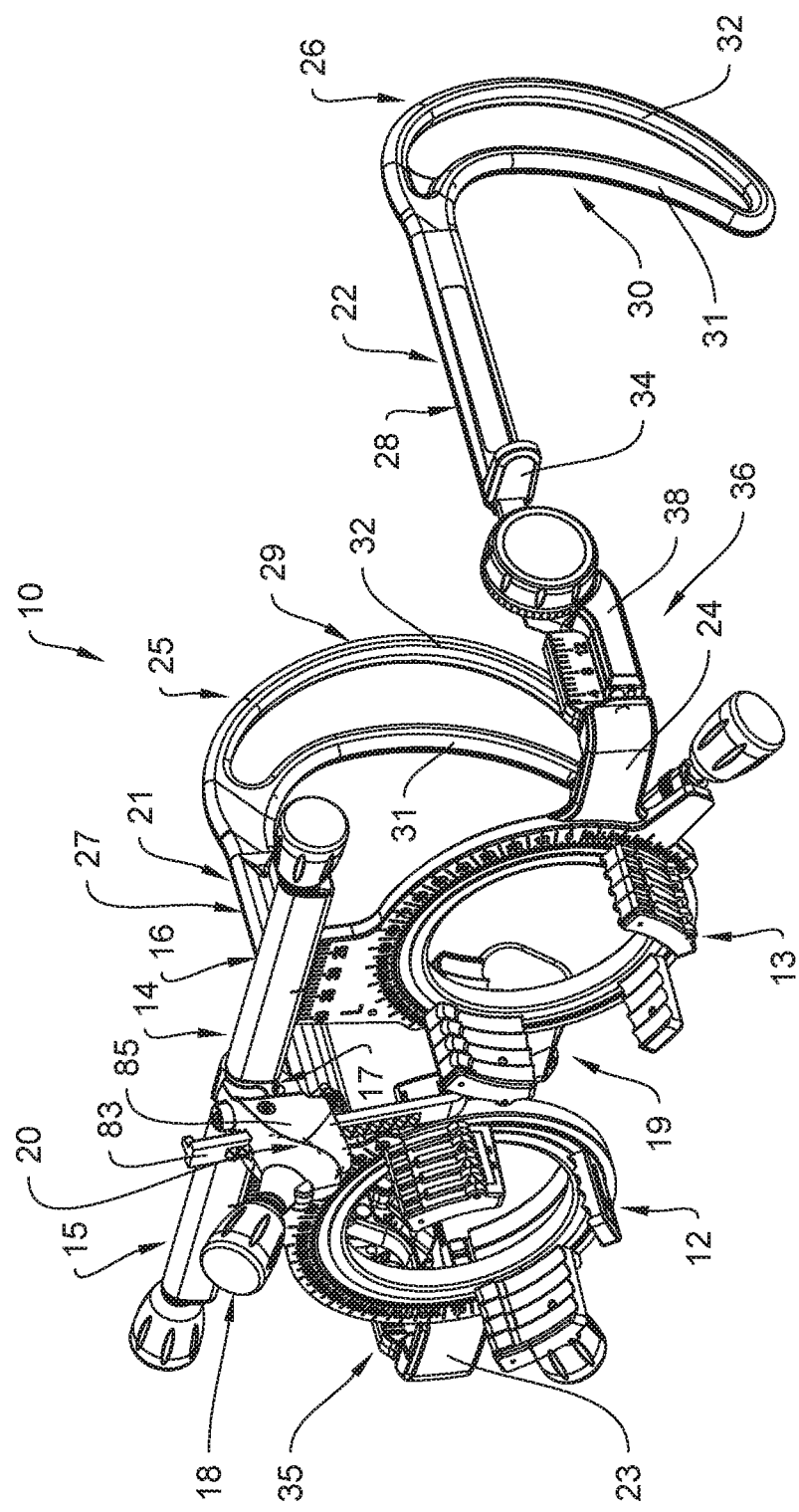
FIG. 1 shows a perspective view of a trial frame.
Figure 2:
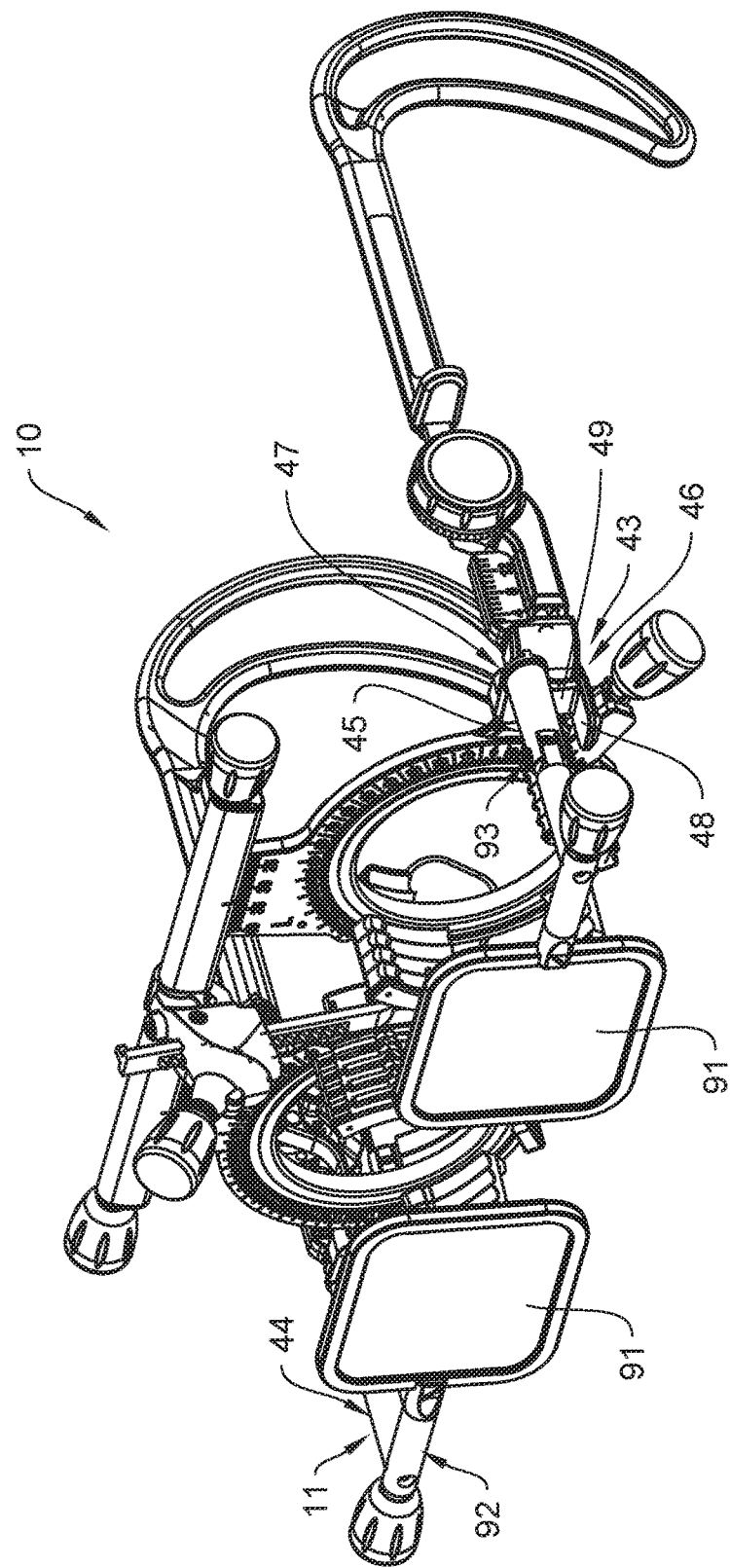
FIG. 2 shows the trial frame with attached polarization filter devices.
Figure 3:
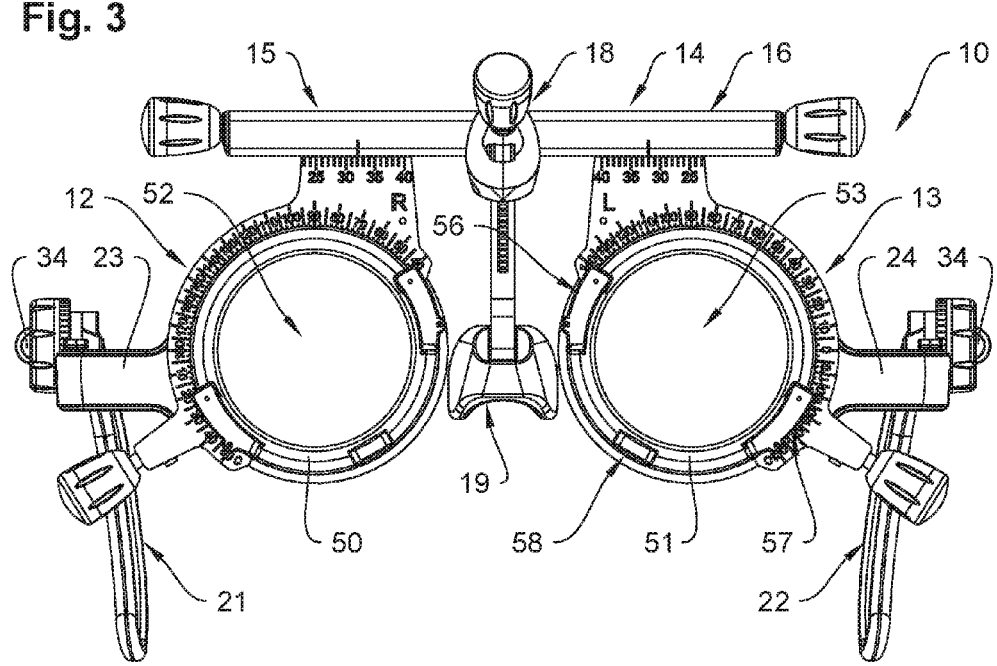
FIG. 3 shows a front view of the trial frame.
Figure 4:
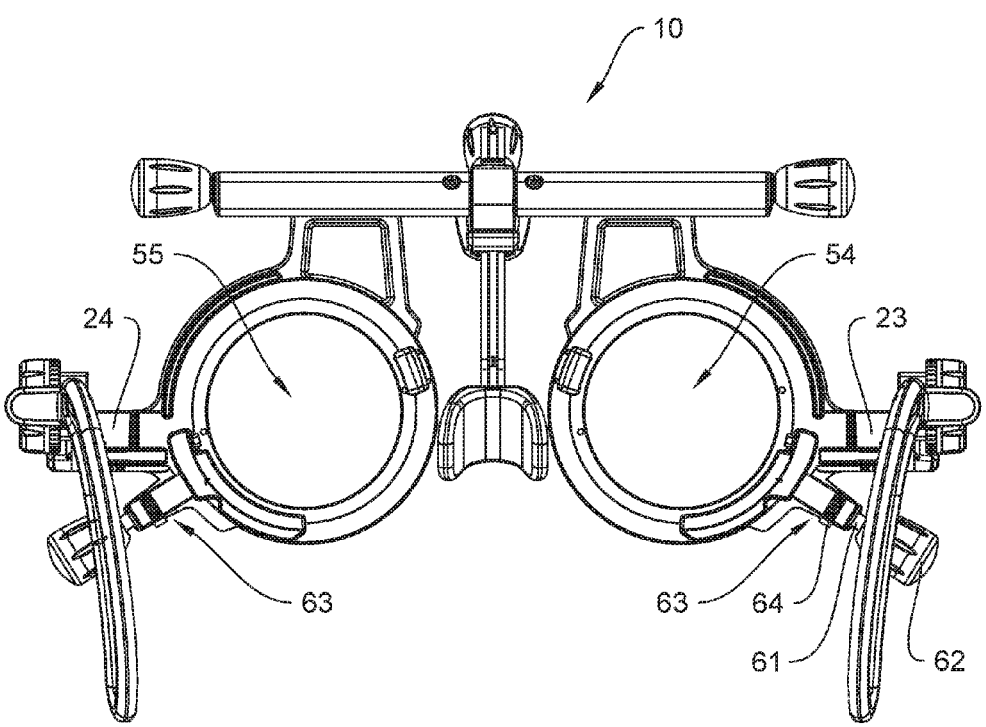
FIG. 4 shows a rear view of the trial frame.
Figure 5:
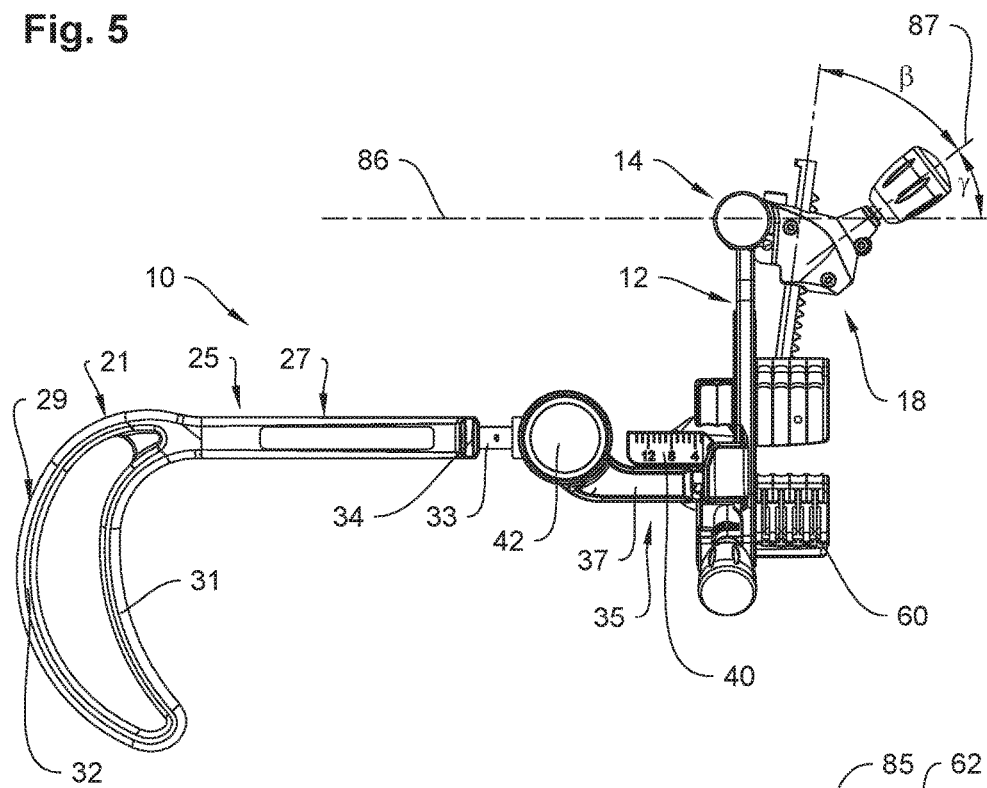
FIG. 5 shows a lateral view of the trial frame.
Figure 6:
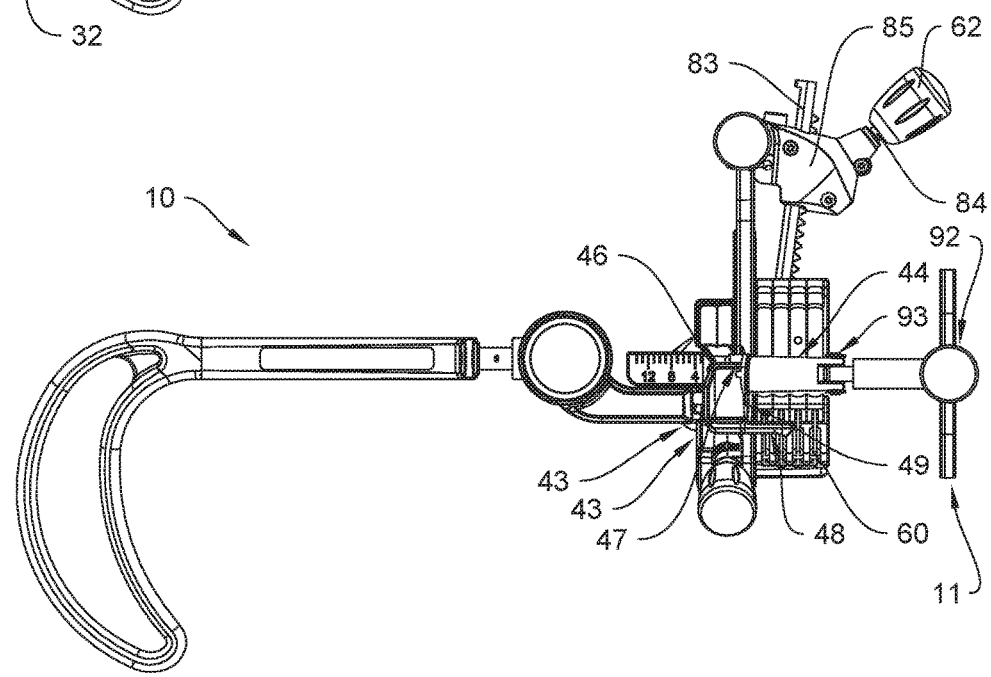
FIG. 6 shows a lateral view of the trial frame with attached polarization filter devices.
Figure 7:
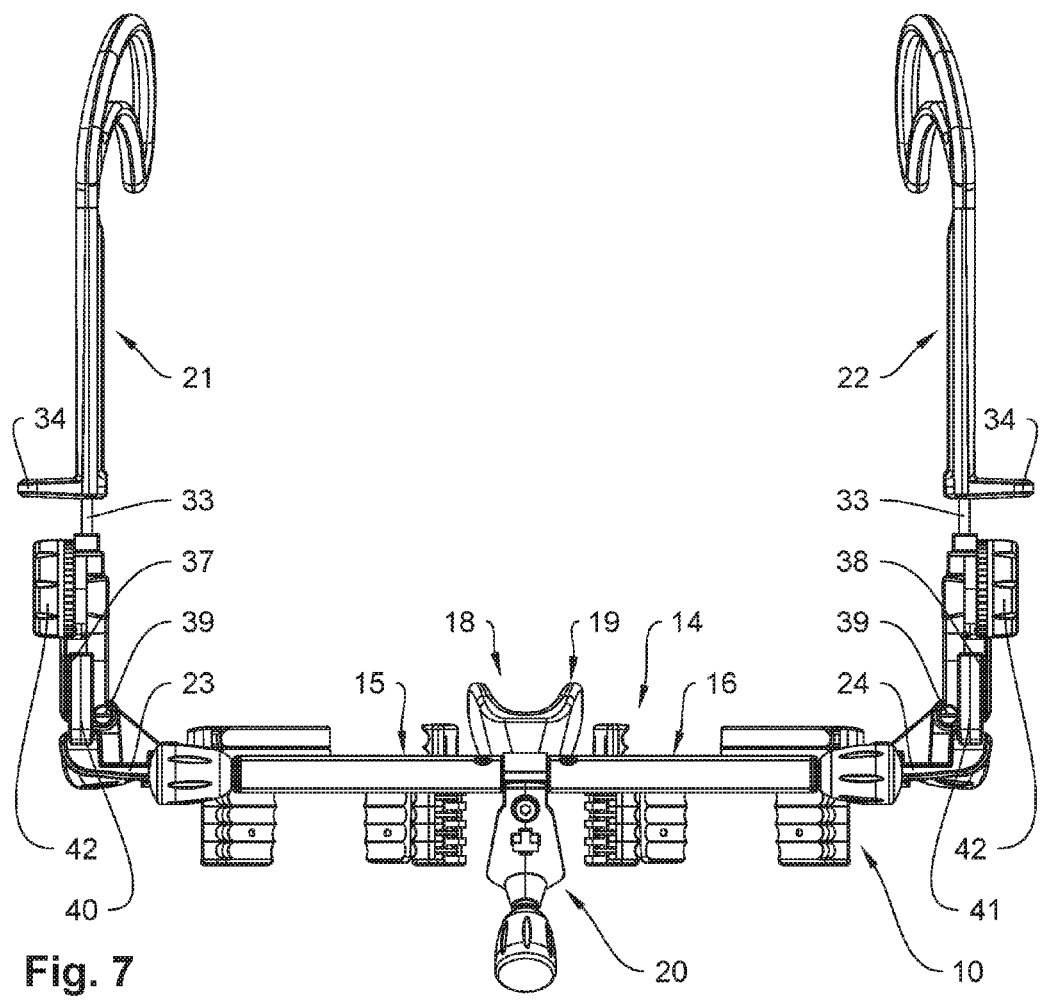
FIG. 7 shows a top view of the trial frame.
Figure 8:
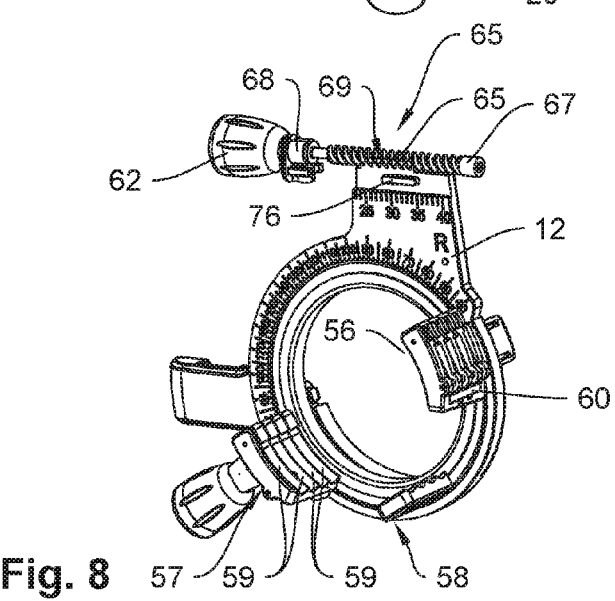
FIG. 8 shows a perspective detail illustration of a lens holder device having a threaded spindle.

A combined view of FIGS. 1 to 7 shows a trial frame 10 in different views. In the illustrations of FIGS. 2 and 6, polarization filter devices 11 of the trial frame 10 are attached to the same. The trial frame 10 serves to determine the subjective refraction of a subject or patient (not illustrated). Hence, directional and positional terms below always relate to body planes of a subject wearing an adjusted trial frame 10. The trial frame 10 comprises two lens holder devices 12 and 13 for receiving insert lenses (not illustrated) and a bridge 14, which connects the lens holder devices 12 and 13 at a distance relative to each other in the transversal direction in an individually adjustable manner. The bridge is formed by two bridge sections 15 and 16, which are firmly connected to each other by means of a pivot axis 17. Accordingly, lens holder device 12 is adjustably attached to bridge section 15 and lens holder device 13 is adjustably attached to bridge section 16. Furthermore, the trial frame 10 comprises a nose rest device 18 having a nose rest 19. The nose rest device 18 or the nose rest 19 is mounted on the pivot axis 17 so as to be radially pivotable in a sagittal plane relative to the bridge 13 or to the lens holder device 12 and 13. Furthermore, the nose rest 19 is height-adjustable in the longitudinal direction relative to the bridge 14 or to the lens holder devices 12 and 13. Height adjustment is made possible by an adjustment gear 20. The trial frame 10 further comprises two temples 21 and 22, which are arranged in a mobile manner on crosspieces 23 and 24 formed by the lens holder devices 12 and 13, respectively. The temples 21 and 22 are length-adjustable relative to the bridge 14 or to the lens holder devices 12 and 13 and height-adjustable in the longitudinal direction.

The temples 21 and 22 have flexible temple ends 25 and 26, respectively, which are formed in one piece together with a temple section 27 and 28, respectively. The temple ends 25 and 26 consist of a soft plastic material and the temple sections 27 and 28 consist of a comparatively hard plastic material. The temple ends 25 and 26 are produced together with the temple sections 27 and 29, respectively, in a shared mold in an injection-molding process. The temple ends 25 and 26 each form a sickle-shaped loop 29 and 30, respectively, ventral loop sections 31 coming into contact with an ear or antihelix and dorsal loop sections 32 ensuring elastic deformation of the temples ends 25 and 26 in the manner of a spring. In this way, the temple ends 25 and 26 adjust particularly well to a subject's ear. The temple sections 27 and 28 are each connected to a guide rod 33 in a longitudinally mobile manner, allowing the temples 21 and 22 to be adjusted in length. To simplify manual length adjustment, actuating protrusions 34 are molded to each of the temple sections 27 and 28. Furthermore, ventral ends 35 and 36 of the temples 21 and 22, respectively, are designed with a cranked section 37 and 38, respectively. The sections 37 and 38 are each pivotably attached to axes 39 at the crosspieces 23 and 24, respectively, translucent rules 40 and 41 being attached to the sections 37 and 38, respectively. The rules 40 and 41 can be used to measure the distance relative to an eye or to its apex. The sections 37 and 38 are further connected to the guide rods 33 via pivot means 42 for adjusting an inclination of the temple ends 24 and 26 in the longitudinal direction. Thus, the temples 21 and 22 can be adjusted and adjusted to a subject's head in three directions, namely transversally, longitudinally and sagittally.

The polarization filter devices 11 are each removably attached to the lens holder devices 12 and 13 by means of a locking connection 43. On holders 44 and 45 of the polarization filter devices 11, one-piece spring clamps 46 are formed, which can be hooked onto the crosspieces 23 and 24 via an upper holding groove 47. Aside from the holding groove 47, the spring clamp 46 has an actuating lever 48, which forms a locking nose (not illustrated). Said locking nose can lock with a locking nose or locking recess (not illustrated, either) below the crosspiece 23 and 24, respectively, the spring clamp 46 engaging behind the crosspieces 23 and 24. The elastic spring clamp 46, which is made of plastic, can be detached from the cross pieces 23 and 24 by pushing the actuating lever 48. In this way, a connecting section 49 of the spring clamp 46, which connects the holding groove 47 to the actuating lever 48, is bent open far enough for the locking connecting 43 to be released and the spring clamp 46 to be removable from the crosspieces 23 and 24. In particular realizing the locking connection 43 under a spring tension caused by the spring clamp makes it possible for the polarization filter devices 11 to be attached to the crosspieces 23 and 24 with zero play and in an easily workable manner.

The polarization filter devices 11 each have a circular or a linear polarization filter 91. The linear polarization filter 91 shown here can be pivoted in and out in front of the lens holder devices 12 and 13 by means of a hinge 93 of the polarization filter device 11. Furthermore, the polarization filter is rotatable in front of the lens holder devices 12 and 13 about an axis 92 of the polarization filter device 11 in such a manner that a direction of polarization of the linear polarization filter 91 can be switched.

The lens holder devices 12 and 13 each have a rotatable ring 50 and 51, respectively, in which four front or ventral lens seats 52 and 53, respectively, are arranged. Furthermore, two rear or dorsal lens seats 54 and 55 are arranged on the lens holder devices 12 and 13, respectively. The front lens seats 52 and 53 are formed by crosspieces 56, 57 and 58, the crosspieces 56 and 57 having pressure fingers 59 for clamping insert lenses (not illustrated). The pressure fingers 59 are subjected to a contact pressure force via a shared leaf spring 60.

Each of the rings 50 and 51 can be manually turned via a rotatable actuating shaft 61 having an operating element 62 and can be adjusted with the aid of a scale division of 2.5° to an angle of a cylinder of an insert lens, for example. To prevent unintentional adjustment of the rings 50 and 51, a braking means 63 is formed on the actuating shaft 61. The braking means 63 is formed by an eccentric plastic ring 64, which surrounds the actuating shaft 61 and by whose radial rotation on the actuating shaft 61 a larger or smaller rotating resistance of the actuating shaft 61 can be set by choice.

A combined view of FIGS. 8 to 12 shows a spindle gear 65 for the lens holder devices 12 and 13, having a threaded spindle 66, an inner bearing 67 and an outer bearing 68 and an operating element 62. A threaded section 69, to which the threaded spindle 66 is engaged, is molded to each of the lens holder devices 12 and 13. A rotation of the threaded spindle 66 consequently causes an adjustment of the lens holder device 12 or 13 in the transversal direction. The bridge sections 15 and 16 are formed by an extruded profile 70 made of aluminum, the extruded profile 70 having a passage bore 71 into which the threaded spindle 66 is inserted with the inner bearing 67. The threaded spindle 66 merely needs to be inserted into the passage bore 71 together with the lens holder devices 12 and 13 and the outer bearing 68 and the inner bearing 67. The outer bearing is secured by means of a screw (not illustrated). A longitudinal slot 72, which forms parallel guide surfaces 73 for side surfaces 74 of the lens holder devices 12 and 13, is connected to the passage bore 71. A guide groove 75 is formed in each of the guide surfaces 73. The lens holder devices 12 and 13 form guide protrusions 76 and 77, which engage into the guide grooves 75. The guide grooves 75 themselves thus form guide surfaces 78 for the guide protrusions 76 and 77. In this way, a particularly stable and zero-play guiding of the lens holder devices 12 and 13 in a thus formed guide means 79 is ensured, the guide means 79 being particularly easy to produce.

All operating elements 62 are always frustoconical and made in one piece of a flexible plastic material, as illustrated by the example of the threaded spindle 66, and are simply plugged onto an actuating end 80. The actuating end 80 has a fitting surface 81 for transmit-ting a torque and a locking recess 82 for securing the operating element 62.

A combined view of FIGS. 13 to 16 shows the adjustment gear 20 of the nose rest device 18 having a toothed rack 83 and a bevel worm wheel 84 and the nose rest 19. The adjustment gear 20 is received in a housing 85 and connected to the pivot axis 17 via said housing 85. The nose rest device 18 is adjusted via the adjustment gear 20 by manual actuation of the operating element 62, which is plugged onto an actuating shaft 88 of the bevel worm wheel 84. The bevel worm wheel 84 has an opening angle α of 90°, the bevel worm wheel 84 thus being arranged at an angle β of 45° relative to the toothed rack 83. As a consequence, the operating element 62 of the bevel worm wheel 84 is always arranged above a transversal plane 86 of the bridge 14. When the nose rest device 18 is adjusted along with the housing 85 on the pivot axis 17 of the bridge 14, a longitudinal axis 87 of the bevel worm wheel 84 is still always inclined by an angle γ>0° in relation to the transversal plane 86. The operating element 62 of the bevel worm wheel 84 is thus always located outside or at the edge of a subject's field of vision and is easily accessible to an operator. Moreover, the position of the operating elements 62 does not interfere with an exchange of insert lenses (not illustrated).

The bevel worm wheel 84 is molded to the actuating shaft 88 in one piece. The operating element 62 is plugged onto the actuating shaft 88. The toothed rack 83 is bent at a lower end 89 and has a receiving axis 90. The nose rest 19, which is made of a flexible plastic material, is merely plugged onto the receiving axis 90. In this way, the nose rest 19 can be easily replaced, if needed.

The invention claimed is:

1. A trial frame for determining the subjective refraction of a subject, comprising:
    first and second lens holder devices for receiving insert lenses;
    a bridge, which connects the first and second lens holder devices in such a manner that their distance relative to each other is adjustable;
    a nose rest device having a pivotable and height-adjustable nose rest;
    first and second temples, which are adjustable in a length and a height dimension, the trial frame comprising first and second polarization filter devices, each of the first and second polarization filter devices having a circular or a linear polarization filter,
and a pivot for pivoting the circular or linear polarization filter in and out in front of the corresponding one of the first and second lens holder devices and a rotating device for rotating the polarization filter in front of the corresponding one of the first and second lens holder devices, the polarization filter devices each being removably attachable to the corresponding one of the first and second lens holder devices through a locking connection; and a one-piece spring clamp formed on an attachment end of a holder of at least one of the polarization filter devices, said spring clamp engaging behind a crosspiece molded to each of the corresponding one of the first and second lens holder devices, and an actuating lever molded to the spring clamp and configured to selectively open the spring clamp.

2. The trial frame according to claim 1, wherein the nose rest device has an adjustment gear for adjusting the height of the nose rest, the adjustment gear having a toothed rack and a bevel worm wheel, which are engaged with each other.

3. The trial frame according to claim 2, wherein the adjustment gear is formed by the toothed rack and the bevel worm wheel.

4. The trial frame according to claim 2, wherein the bevel worm wheel has an opening angle α of 60° to 120°.

5. The trial frame according to claim 4 wherein the bevel worm wheel has an opening angle α of 90°.

6. The trial frame according to claim 2, wherein the bevel worm wheel has a lead of 1 mm to 3 mm.

7. The trial frame according to claim 6, wherein the bevel worm wheel has a lead of 2 mm.

8. The trial frame according to claim 2, wherein the bevel worm wheel is molded to an actuating shaft, wherein an operating element can be plugged onto the actuating shaft.

9. The trial frame according to claim 8, wherein the operating element is arranged above the bridge.

10. The trial frame according to claim 8, wherein the operating element is cylindrical or frustoconical in shape and is made in one piece of a flexible plastic material.

11. The trial frame according to claim 1 wherein the nose rest device is mounted on a pivot axis of the bridge with a radial clamping.

12. The trial frame according claim 1 wherein the bridge is formed by first and second bridge sections, which are firmly connected with a pivot axis, the nose rest device being pivotably mounted on the pivot axis.

13. The trial frame according claim 1 wherein the bridge and the first and second lens holder devices together form a guide for guiding the first and second adjustable lens holder devices in the longitudinal direction of the bridge, the bridge having a spindle gear including a threaded spindle for distance adjustment of the first and second lens holder devices, at least one guide protrusion being formed on each of the first and second lens holder devices which engages into a guide groove formed in the bridge, open threaded sections being formed on each of the first and second lens holder devices, the threaded spindle being engaged with the threaded section.

14. The trial frame according to claim 1 wherein the first and second lens holder devices each have a rotatable ring, on which corresponding first and second lens seats are formed, an actuating shaft of each ring having an adjustable brake comprising an eccentric plastic ring.

15. The trial frame according to claim 1 wherein the first and second lens holder devices each have four front and two rear lens seats.

16. The trial frame according to claim 1 wherein each lens seat of the first and second lens holder devices has at least one pressure finger for clamping an insert lens, the respective pressure fingers being arranged in a row on the lens holder device and being subjectable to a contact pressure force via a shared leaf spring.

17. The trial frame according to claim 1 wherein each temple end of the first and second temples is flexible and loop-shaped.

18. The trial frame according to claim 1 wherein each temple end of the first and second temples is formed in one piece and a portion is made of a soft plastic and a portion is made of a hard plastic material.

19. The trial frame according to claim 1 wherein a ventral end of the temple is cranked.

* * * * *